US012797590B2

(12) United States Patent
Sutherland

(10) Patent No.: US 12,797,590 B2
(45) Date of Patent: Nov. 17, 2026

(54) PULMONARY ARTERIAL COMPLIANCE ENHANCEMENT AND CONTROL DEVICE

(71) Applicant: Corvia Medical, Inc., Tewksbury, MA (US)

(72) Inventor: Michael Warren Sutherland, Tewksbury, MA (US)

(73) Assignee: Corvia Medical, Inc., Tewksbury, MA (US)

( * ) Notice: Subject to any disclaimer, the term of this patent is extended or adjusted under 35 U.S.C. 154(b) by 204 days.

(21) Appl. No.: 18/746,530

(22) Filed: Jun. 18, 2024

(65) Prior Publication Data

US 2024/0335642 A1 Oct. 10, 2024

Related U.S. Application Data

(63) Continuation of application No. 18/062,725, filed on Dec. 7, 2022, which is a continuation of application
(Continued)

(51) Int. Cl.

| | |
|---|---|
| ***A61M 25/10*** | (2013.01) |
| ***A61M 25/00*** | (2006.01) |
| *A61F 2/01* | (2006.01) |

(52) U.S. Cl.
CPC .... *A61M 25/1018* (2013.01); *A61M 25/0023* (2013.01); *A61F 2/011* (2020.05);
(Continued)

(58) Field of Classification Search
CPC .......... A61M 25/1018; A61M 25/0023; A61M 2210/125; A61M 1/3655; A61M 27/002; A61M 2205/3334; A61M 2205/3331; A61M 1/3656; A61M 1/3653; A61M 1/36; A61M 60/148; A61M 5/1723; A61F 2/011; A61F 2/02; A61F 2/04; A61F 2/06; A61F 2002/061; A61F 2/064; A61F 2002/065; A61F 2002/068; A61F 2/07; A61F 2002/072; A61F 2002/075; A61F 2002/077; A61F 2/82; A61F 2/90; A61F 2/95; A61F 2/958; A61F 2/915; A61F 2210/0076;
(Continued)

(56) References Cited

U.S. PATENT DOCUMENTS

| | | | | | |
|---|---|---|---|---|---|
| 2013/0204176 | A1* | 8/2013 | Duffy | .................. | A61M 1/3655 604/9 |
| 2026/0007407 | A1* | 1/2026 | Chang | .................... | A61B 17/11 |

* cited by examiner

*Primary Examiner* — Tan-Uyen T Ho
*Assistant Examiner* — Bridget E. Rabaglia
(74) *Attorney, Agent, or Firm* — Goodwin Procter LLP

(57) ABSTRACT

Devices and methods for increasing a patient's pulmonary arterial compliance are disclosed. The devices include catheters designed to create a connection between a patient's venous anatomy and the patient's pulmonary artery. With the arteriovenous connection various devices can be implanted in order to increase the volumetric compliance of the pulmonary artery. The devices include collapsible and expandable mechanisms which allow the effective pulmonary arterial volume to expand during systole and contract during diastole. The devices may include a balloon or balloon-like implants which cyclically shuttle a working fluid from the pulmonary artery to the vein and back. The devices may be adjustable to provide desired hemodynamic benefits. Methods are disclosed for making and using the inventive devices.

20 Claims, 7 Drawing Sheets

Related U.S. Application Data

No. 16/579,787, filed on Sep. 23, 2019, now abandoned.

(60) Provisional application No. 62/735,623, filed on Sep. 24, 2018.

(52) U.S. Cl.
CPC ............... *A61M 2025/0024* (2013.01); *A61M 2025/0025* (2013.01); *A61M 2210/125* (2013.01)

(58) Field of Classification Search
CPC ............ A61F 2/2418; A61F 2230/0069; A61F 2/2412; A61F 2220/0016; A61F 2/013; A61F 2210/0014; A61B 17/12172; A61B 17/12036; A61B 17/12136; A61B 2017/1107; A61B 2017/1139; A61B 17/12109; A61B 17/12031
See application file for complete search history.

PULMONARY ARTERIAL COMPLIANCE ENHANCEMENT AND CONTROL DEVICE

CROSS-REFERENCE TO RELATED APPLICATION

This application is a continuation of U.S. application Ser. No. 18/062,725, filed Dec. 7, 2022, which is a continuation of U.S. application Ser. No. 16/579,787, filed Sep. 23, 2019, which claims the benefit of U.S. Application No. 62/735,623, filed on Sep. 24, 2018, which is incorporated herein in their entirety by reference.

FIELD

The present invention relates to methods and devices for pulmonary hypertension and heart failure. In particular, the present invention relates to methods and devices for treating pulmonary hypertension by increasing the pulmonary arterial compliance and thereby reducing the right ventricle after-load.

BACKGROUND

Heart failure is a condition effecting millions of people worldwide. Right-sided and left-sided heart failure can both lead to pulmonary hypertension which can in-turn lead to right heart failure. There exists a need for devices and methods for treating pulmonary arterial hypertension and right heart failure. Pulmonary arterial hypertension is described by increased pulmonary vascular resistance and decreased pulmonary arterial compliance. While methods of treating increased pulmonary vascular resistance may include pharmacological treatments or diuretics there exists a need for treating decreased pulmonary arterial compliance. To that end devices and methods are disclosed that increase the volumetric pulmonary arterial compliance in order to reduce the right ventricular after-load and to treat heart failure.

SUMMARY OF THE DISCLOSURE

In general, the present invention concerns treating right heart failure and pulmonary hypertension. To this end, devices and methods are disclosed herein which may include implanting a compliant element to the pulmonary arterial trunk and left and right pulmonary arteries to increase the volumetric compliance of the pulmonary arterial vasculature. Furthermore, devices and methods are disclosed herein for treating pulmonary hypertension which may include accessing the pulmonary artery trunk, delivery an implant and adjusting the implant as needed to increase the compliance of the pulmonary artery and reduce the after-load on the right ventricle. Additionally, devices and methods are disclosed which may include implanting a device inside a patient's pulmonary artery in order to increase the volumetric compliance of the pulmonary artery and providing a means for adjusting the amount of volumetric compliance of the artery and further providing a means for repositioning, retrieving, or removing the implant as needed to treat a patient.

In some embodiments, an implantable compliant device is provided.

DETAILED DESCRIPTION

Certain specific details are set forth in the following description and FIGS. to provide an understanding of various embodiments. Those of ordinary skill in the relevant art will understand that they can practice other embodiments without one or more of the details described below. Further, while various processes are described herein with reference to steps and sequences, the steps and sequences of steps are not to be understood as being required to practice all embodiments of the present invention.

Unless otherwise defined, explicitly or implicitly by usage herein, all technical and scientific terms used herein have the same meaning as those which are commonly understood by one of ordinary skill in the art to which this present invention pertains. Methods and materials similar or equivalent to those described herein may be used in the practice or testing of the present invention. In case of conflict between a common meaning and a definition presented in this document, latter definition will control. The materials, methods, and examples presented herein are illustrative only and not intended to be limiting.

Unless expressly stated otherwise, the term "embodiment" as used herein refers to an embodiment of the present invention.

Unless a different point of reference is clear from the context in which they are used, the point of reference for the terms "proximal" and "distal" is to be understood as being the position of a practitioner who would be implanting, is implanting, or had implanted a device into a patient's anatomy. An example of a context when a different point of reference is implied is when the description involves radial distances away from the longitudinal axis or center of a device, in which case the point of reference is the longitudinal axis or center so that "proximal" refers to locations which are nearer to the longitudinal axis or center and "distal" to locations which are more distant from the longitudinal axis or center.

As used herein, the terms "subject" and "patient" refer to any animal, such as a mammal like livestock, pets, or humans. Specific examples of "subjects" and "patients" include, but are not limited, to individuals requiring medical assistance, and requiring treatment for symptoms of heart failure.

Figure 1:
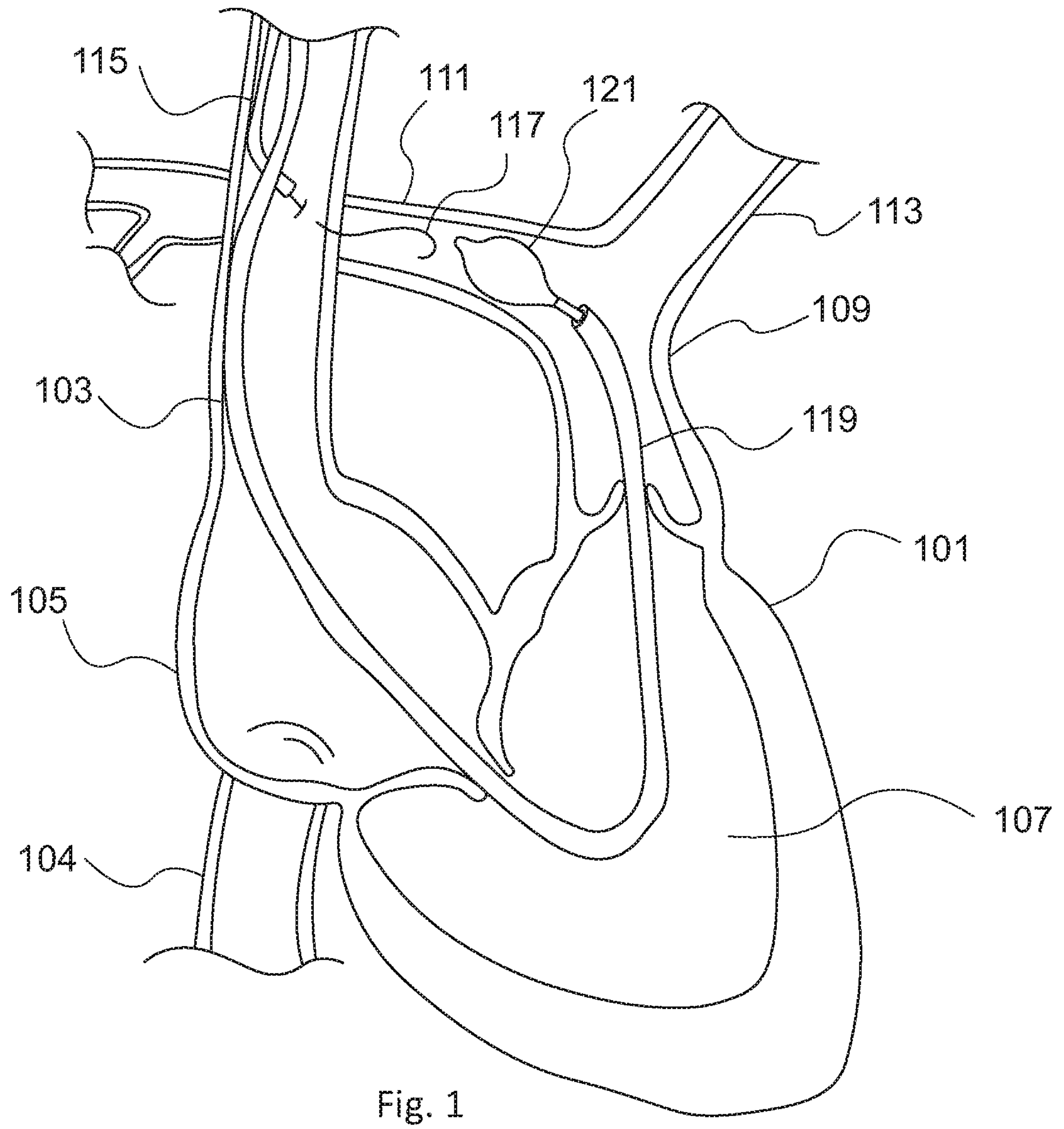
FIG. 1 depicts a cross-sectional view of a patient's heart having an exemplary venous wiring catheter in the SVC and an exemplary snare catheter according to some embodiments of the present teachings.

FIG. 1 depicts a cross-sectional view of a patient's heart 101 including a superior vena cava 103 (SVC), an inferior vena cava 104 (IVC), a right atrium 105 (RA), a right ventricle 107 (RV), and a pulmonary artery 109 (PA). The pulmonary artery includes a right branch 111 and a left branch 113. A venous wiring catheter 115 is shown in the SVC and directed towards the right branch of the pulmonary artery. The catheter is configured to allow for directional control of the catheter tip and is configured to deliver a wire 117 through the wall of the SVC and into the lumen of the pulmonary artery. The wire is depicted having crossed into the pulmonary artery. A second pulmonary artery catheter 119 is depicted and has been threaded through the SVC, through the right atrium and right ventricle and into the pulmonary artery trunk. This catheter is configured to allow for passage of a snaring catheter 121 to snare the wire in the pulmonary artery. In this manner the catheters of FIG. 1 represent a means for creating an initial puncture from the SVC into the pulmonary artery and for being able to access that puncture from the SVC and from the pulmonary artery.

The venous wiring catheter of FIG. 1 may be configured to be steerable or articulating, for example, by using a pull wire to generate a predetermined curve when the wire is tensioned. The venous wiring catheter of FIG. 1 may feature a pre-determined curved shape useful for pointing towards the PA. The wiring catheter may be made out of any suitable material or construction including Nylon, PEBAX, polyethylene, polyurethane, PEEK, or any other polymeric material. The wiring catheter may include wound or braided support structures including braided stainless steel. The wiring catheter may be configured with an internal diameter of between 0.5 mm and 1.5 mm.

The wire of FIG. 1 may be made from any suitable material. For example, the wire may be made from Nitinol or stainless steel. The wire may include a sharpened distal segment for penetrating the vein and artery. The wire may include a flexible segment just proximal to the distal tip such that when supported by the delivery catheter the wire has sufficient column strength to cross the vessel walls but once through the walls the wire is not able to further cross back outside the pulmonary artery. The wire may be configured with a helical coil tip such that torque may be used to force the wire across the vessel walls. The wire may instead be replaced by an off the shelf component such as a Brockenbrough needle or similar device. The wire may instead be a needle like assembly, for example, a laser cut hypotube may be used as a vessel crossing wire. The wire may be configured to deliver energy in order to cross the vessel walls, for example, electrical energy, RF energy, or heat energy may be used to assist the wire crossing.

The pulmonary artery catheter of FIG. 1 may be made from any of the same materials or constructions as described above. The pulmonary artery catheter may feature a predetermined shape useful for accessing the pulmonary artery. The pulmonary artery catheter may be configured to ride over an interventional wire or balloon catheter, such as a Swan-Ganz catheter. The pulmonary artery catheter may be any reasonable size and length. For example, the pulmonary artery catheter may be 80 cm long and feature an outer diameter of approximately 5 mm and an internal diameter of 3.5 mm. The pulmonary artery catheter may have deflecting or articulating segments, for example, curves that can be adjusted with the use of an internal pull wire. The pulmonary artery catheter is configured to create a lumen through which additional devices may be delivered to the pulmonary artery. For example, as shown in FIG. 1, the pulmonary artery catheter may be configured to deliver a snare which can be used to capture and externalize the vessel crossing wire. Once externalized the wire and pulmonary artery catheter can be used to deliver a pulmonary artery compliance enhancement device as described herein.

The snare of FIG. 1 may be a custom basket snare designed to fill the internal diameter of the pulmonary artery. The snare of FIG. 1 one may be a simple goose-neck snare. The snare of FIG. 1 may instead be a commercially available vascular snare.

FIG. 1 depicts a method for creating a connection from the SVC to the PA in a patient. This connection may then be used to deliver additional inventive devices or embodiments of the present invention, for example, a device may be delivered over the wire and into the pulmonary artery which effectively increases the volumetric compliance of the pulmonary artery. In some embodiments once the wire has been snared and externalized an enlarged pathway or shunt may be created between the superior vena cava and the pulmonary artery. In some embodiments the enlarged pathway is created by advancing a dilating catheter over the wire. In embodiments the enlarged pathway or shunt is created by cutting the tissue surrounding the wire or ablating the tissue around the wire.

Figure 2:
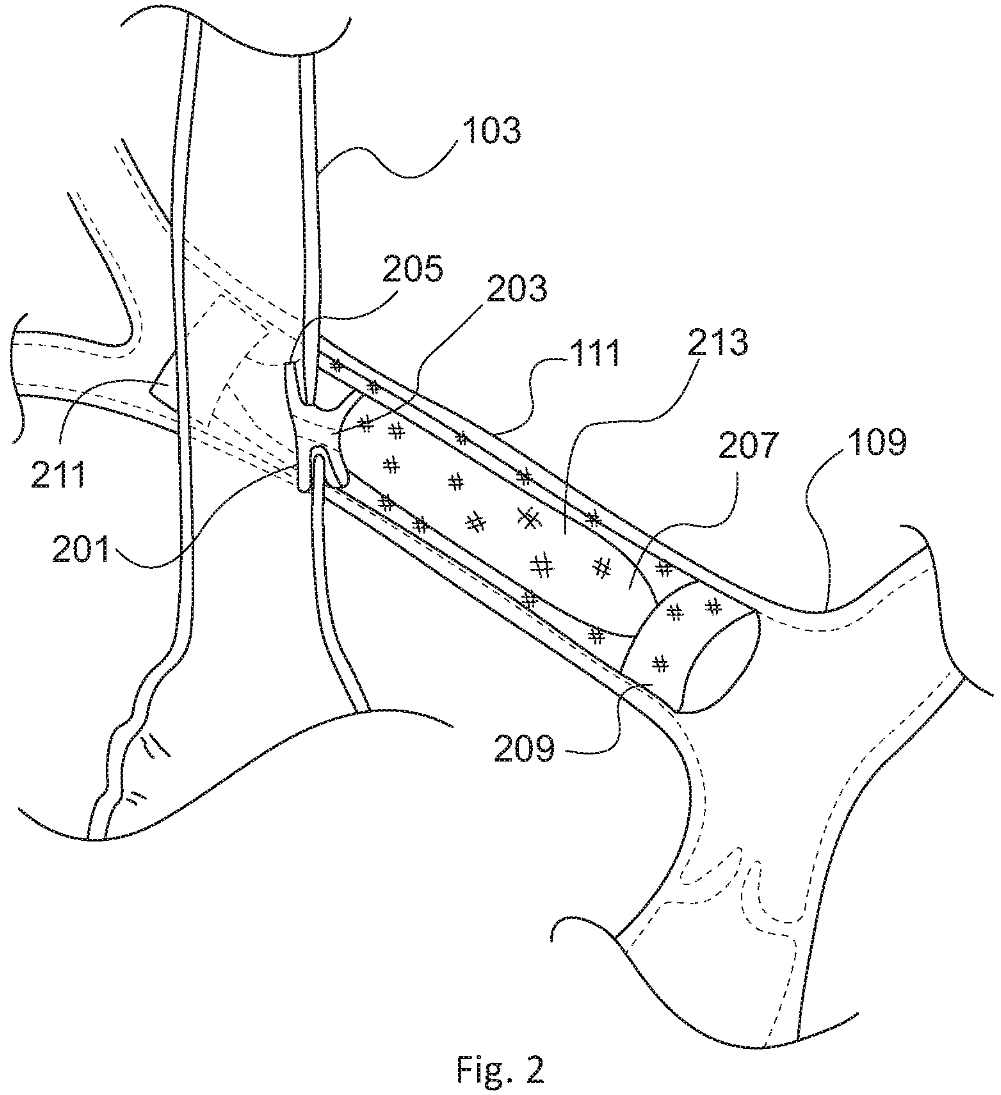
FIG. 2 illustrates an exemplary device implanted between the superior vena cava and pulmonary artery according to some embodiments of the present teachings.

Turning now to FIG. 2, a patient's superior vena cava 103 and pulmonary artery 109 are depicted. A shunting device 201 has been implanted; creating a pathway between the superior vena cava and the right branch 111 of the pulmonary artery. The shunting device includes a tubular body 203 with an internal diameter for fluid passage and a number of anchoring arms 205. The shunting device is configured to allow blood or fluid to flow through the internal diameter of the shunting device and to prevent blood from passing around the arms of the shunting device or into the space between the vessels. A stent-like compliant implant 207 resides in the pulmonary artery. The stent like compliant implant includes a metallic skeleton structure (not shown) and a thin covering film. The compliant implant includes a proximal anchoring section 209 and a distal anchoring section 211. The proximal and distal anchoring section are designed to anchor the implant to the internal walls of the pulmonary artery and to prevent blood flow around the edges of the implant. The compliant implant includes a reversibly collapsible and expandable segment 213 between the two anchoring segments.

The shunting device of FIG. 2 may be configured to be delivered in a collapsed state and then expanded or allowed to expand into position in a previously created shunt between the SVC and pulmonary artery. The shunting device of FIG. 2 may be made from a single laser cut super-elastic or shape memory nitinol hypotube. The shunting device may be made from any suitable material, including Nitinol, stainless steel, polyurethane, PET, PEEK, cobalt chromium alloys, or other metallic materials, alloys, or polymeric materials. The shunting device may be made from two telescoping halves, an arterial half and a venous half. The shunting device may be covered by a fabric or film in order to improve haemostatic sealing against the vessel walls. The shunting device may instead by covered by a mammalian pericardium such as bovine pericardium. The covering may be sewn to the shunting device at predetermined attachment points. The shunting device may include elements designed to compress the wall of the vessels together. The shunting device may include secondary anchoring elements, such as barbs or hooks which engage the vessel walls. The internal diameter of the shunting device may be configured to allow sufficient fluid flow through the device such that during systole the collapsible portion of the compliant implant is allowed to collapse and force fluid through the shunt and during diastole the compliant implant is allowed to return to its pre-determined lower energy state. For example, the internal diameter of the shunting device may be between 4 mm and 10 mm.

The shunting device may be delivered over a wire which has been passed through the vessel walls, such as depicted in FIG. 1. The shunting device may be configured to forcibly expand the passageway between the superior vena cava and the pulmonary artery. The shunting device may be delivered from the superior vena cava side or from the pulmonary artery side or from both sides in a stepwise or simultaneous manner.

The compliant implant may include a skeleton structure that is made from any suitable material including any of the materials referenced above. The compliant implant may include a covering material such as a film, fabric, or other cover. The compliant implant may be covered in a similar manner to a covered stent, for example, a covered stent used to treat abdominal aortic aneurysms. The compliant implant may be covered by a thin film of expanded PTFE material. The compliant implant may be covered by a hydrogel material. The covering may be sewn to the stent-like implant at various attachment points. In embodiments the compliant implant includes a skeleton structure made from a laser cut Nitinol hypotube which has been expanded and heat set to a suitable outer diameter. In embodiments an ePTFE film is attached to the expanded Nitinol tube. In some embodiments the skeleton structure is a woven or laser cut stainless steel structure which is expanded into position by inflating a balloon inside the structure. The anchoring segments of the implant may include additional compliant material adapted for creating a haemostatic seal around the internal diameter of the artery. In some embodiments the anchoring segment includes a folded up skirting material which helps to seal the ends of the device to the vessel wall. The compliant implant may include a substantially flattened section, which is configured to hold a flattened shape under a first amount of internal blood pressure and which is configured to expand to a rounded shape under a second higher amount of internal blood pressure. In embodiments this first and second pressures can be adjusted by incorporating pull wires or stiffening wires into the structure of the implant. The compliant implant is configured to take up as much length of the right branch of the pulmonary artery as possible while not blocking any of the distal pulmonary artery passages. For example, the compliant implant may be 6 cm long. The compliant implant may be keyed to the shunting device such that the collapsible portion of the implant substantially faces the shunting device. The shunting device may protrude into the pulmonary artery enough such that when the compliant implant expands due to the systolic pressure wave the expansion around the shunt is limited, thereby allowing the fluid to be forced through the shunt and preventing the compliant implant from prematurely closing off the fluid path created by the shunt.

The compliant implant and shunting device of FIG. 2 combine to increase the effective pulmonary arterial volumetric compliance. The internal fluid volume of compliant implant is designed to expand during cardiac systole and return to its low energy state during cardiac diastole.

Figure 3:
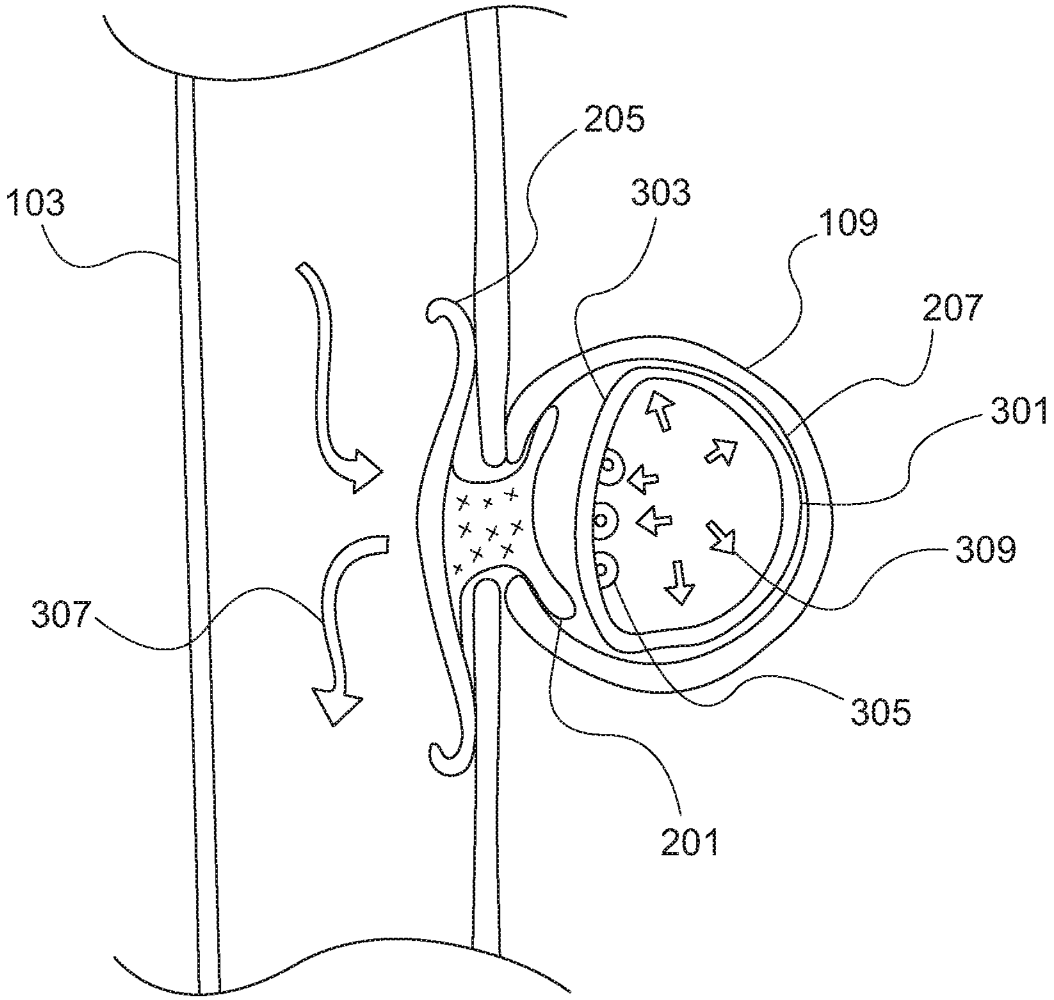
FIG. 3 illustrates an exemplary device implanted between the superior vena cava and pulmonary artery according to some embodiments of the present teachings.

Turning now to FIG. 3 embodiments of the present invention are depicted. A patient's superior vena cava 103 and pulmonary artery 109 are shown in cross section. A shunting device 201 has created a passageway between the SVC and the pulmonary artery. The shunting device includes a plurality of anchoring arms 205 on the venous and arterial sides of the shunt. A cross section of a compliant stent-like implant 207 is shown residing inside the pulmonary artery. The compliant implant includes a generally round wall segment 301 and a substantially flattened wall segment 303. The substantially flattened wall segment represents a reversibly collapsible and expandable segment as described above. The compliant implant includes proximal and distal anchoring segments (not shown) which have a generally round cylindrical shape and which prevent blood from flowing from the pulmonary artery around the device. A series of tubular extrusions 305 are incorporated into the wall of the compliant implant and are shown in cross-section. Large arrows 307 are shown to depict the flow of blood into and out of the shunting device. Smaller arrows 309 are shown to depict the outward force on the compliant device caused by the pulmonary artery pressure wave.

The compliant implant of FIG. 3 is configured to reversibly expand and collapse during a patient's cardiac cycle. For example, during systole the flattened wall of the compliant implant is configured to expand and substantially fill the space of the pulmonary artery, in the process forcing blood or fluid (saline, radio-opaque contrast, etc.) through the shunting device. During diastole the flattened wall is configured to return to its lower energy shape as depicted in FIG. 3. The compliant implant may be made from any of the materials as described above. For example, the compliant implant may be made from a laser cut Nitinol hypotube which has been heat set into the desired shape. The compliant implant may include a covering material such as described above. For example, the compliant implant may be entirely covered by a sheath of expanded PTFE polymer. In some embodiments the compliant implant is made of or surrounded by a wall of hydrogel material. In some embodiments the compliant implant is made entirely by a specially shaped, implantable, thin walled, annular balloon.

The tubular extrusions of FIG. 3 are configured for accepting a number of stiffening bars as necessary. For example, a single stiffening bar may be inserted in the central tubular extrusion for some patients, while other patients may require the use of all three stiffening bars. In this manner the tubular extrusions and stiffening bars represent a means for adjusting the pressure differential required to collapse and expand the compliant implant. The stiffening bars may be made from any suitable material including stainless steel, Nitinol, PEEK, polyimide, polyurethane, PTFE, FEP, ultra-high molecular weight polyethylene, cobalt-chromium alloys, or other metallic alloys or polymeric materials. The stiffening bars may be braided or twisted cables. The stiffening bars may feature composite construction, for example, a stainless steel coil wrapped around a central elastic tensile member may be used. The stiffening bars may be made from laser cut tubing material, for example, a laser cut Nitinol hypotube may be used or a laser cut stainless steel tube may be used. In embodiments the stiffening bar and tubular extrusion may instead be a stacked stainless steel coil, the coil being sewn into or otherwise attached to the compliant implant. Through the coil an elastic tensioning member resides. The elastic tensioning member may be made from any suitable material including UHMWPE, PET, polyurethane, silicone rubber, or other materials. The elastic tensioning member may feature braided or twisted strands. The elastic tensioning member may feature a high stiffness or elastic modulus and is configured to undergo primarily elastic elongation under a predetermined amount of tension. The tensioning member is fixedly attached to the distal end of the stacked coil. The tensioning member and stacked coil are configured such that an amount of tension may be applied to the tensioning member, thereby compressing the stacked coil. This tension may be locked in by a secondary locking element, such as a sliding knot, a crimped tube, or a cam or ratcheting mechanism. The amount of tension on the tensioning member can be adjusted in order to vary the bending stiffness of the stacked coil arrangement. In this way the stacked coil and tensioning member represent a means for adjusting the stiffness of the substantially flat walled section of the compliant implant. This adjustable stiffness of the compliant implant in turn adjusts the amount of differential pressure required to collapse or expand the compliant implant. In embodiments the tubular extrusions of FIG. 3 may be configured to support an elongate, inflatable compliant or non-compliant balloon. The amount of pressure used to inflate the balloon can be varied, for example, significant pressure can be applied to the fluid in the balloon thereby increasing the stiffness of the collapsible portion of the compliant implant. In some embodiments the amount of fluid used to inflate the stiffening balloons may be adjusted by a user in order to create a collapsible implant with a predetermined stiffness and which collapsed at a desired pressure differential.

The shunting device of FIG. 3 may be made of any of the materials and constructions as described above. The shunting device may be substantially similar to the shunting device depicted in FIG. 2.

Figure 4:
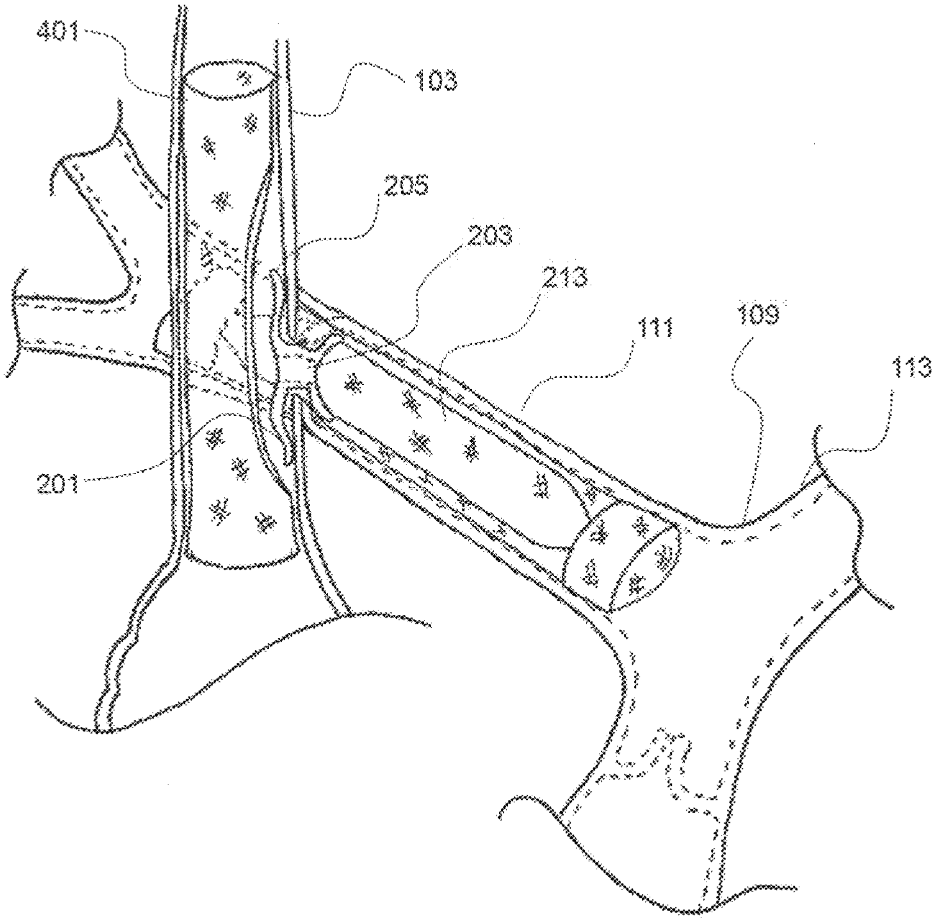
FIG. 4 illustrates an exemplary device implanted between the superior vena cava and pulmonary artery according to some embodiments of the present teachings.

Turning now to FIG. 4, embodiments of the present invention are depicted. A patient's superior vena cava 103 and pulmonary artery 109 are depicted. The pulmonary artery has a left branch 113 and a right branch 111. A shunting device 201 with a tubular body 203 and anchoring arms 205 has been implanted into a shunt that was created between the SVC and the pulmonary artery. A stent-like compliant implant 207 with proximal anchoring section 209, distal anchoring section 211, and reversibly expandable section 213 has been deployed in the pulmonary artery. A venous compliant implant 401 has been deployed in the superior vena cava. The venous compliant implant may include a proximal anchoring section and a distal anchoring section. The anchoring sections are designed to fix the implant to the inner walls of the SVC as well as to prevent fluid flow around the ends of the device. The venous compliant implant may be made in the same manner and with the same materials as the stent-like compliant implant in the pulmonary artery. The venous compliant implant may have a stent-like skeleton structure (not shown) and a covering element. The venous compliant implant may be manufactured in a manner similar to that of a covered stent. The venous compliant implant may be manufactured in a manner similar to that of a covered stent designed to treat aortic abdominal aneurysms. The venous compliant implant includes a reversibly collapsible section between the two anchoring sections. The reversibly collapsible section may have an adjustable stiffness, using for example, pull wires or stiffening bars to adjust the stiffness of the collapsible segment.

The venous compliant implant of FIG. 4 may be delivered using a delivery catheter. The venous compliant implant may be delivered in a collapsed configuration and allowed to expand in the SVC. The venous compliant implant may be delivered in a collapsed configuration and expanded mechanically, for example, with the use of a balloon catheter. The venous compliant implant may be keyed in delivery such that the reversibly collapsible segment faces the shunting device.

The complaint implants and shunting device of FIG. 4 together create a haemostatic fluid reservoir inside the patient's vasculature. After delivery of the implants the blood volume may be removed from the haemostatic fluid reservoir and replaced with saline. In embodiments the venous compliant delivery device is delivered alongside a small fluid exchange catheter. The fluid exchange catheter is configured to substantially replace any fluid in the haemostatic reservoir with saline or with a mixture of saline and radio-opaque contrast medium. In embodiments the amount of fluid injected into the haemostatic region is adjusted in order to control the relative pressure in the haemostatic region. In embodiments fluid is injected into the haemostatic fluid reservoir until the venous compliant device collapses a pre-determined amount. In embodiments fluid is injected into the haemostatic fluid reservoir until a desired amount of fluid volume cycles from the arterial side of the reservoir to the venous side of the reservoir during each cardiac cycle. In some embodiments the venous compliant implant includes an elongate fluid filling port which can be used to fill the haemostatic fluid reservoir. In some embodiments the fluid filling port is configured to releasably engage with a fluid filling catheter. For example, after implantation a first amount of fluid can be injected into the haemostatic fluid reservoir and the catheters may be removed. In subsequent procedures the fluid filling port could then be engaged by a filling catheter, for example, by snaring the fluid filling port and then advancing the filling catheter over the snare until it engages the fluid filling port. In this way the compliant implants and fluid filling ports could be used to adjust the amount of fluid injected into the haemostatic fluid reservoir as desired by a clinician.

The compliant implants and shunting device of FIG. 4 represent a means for increasing the volumetric compliance of the pulmonary artery. The compliant implants are configured to reversibly expand and collapse, thereby changing the internal blood volume in the region of the implants. The compliant implants are further configured to expand and collapse at predetermined cardiac pressures. In embodiments the pressure differential required to expand and collapse the compliant implants is adjustable by a clinical user.

In some embodiments the compliant implants and shunting device may be connected to a separate pump. For example, a fluid pump could be implanted under the skin in a similar manner to a pacemaker. An implantable fluid delivery catheter could connect the implanted pump to the compliant implants. The implantable pump would then be configured to cyclically pump fluid into the reservoir during desired points in the cardiac cycle in order to increase the effective compliance of the pulmonary arteries.

Figure 5:
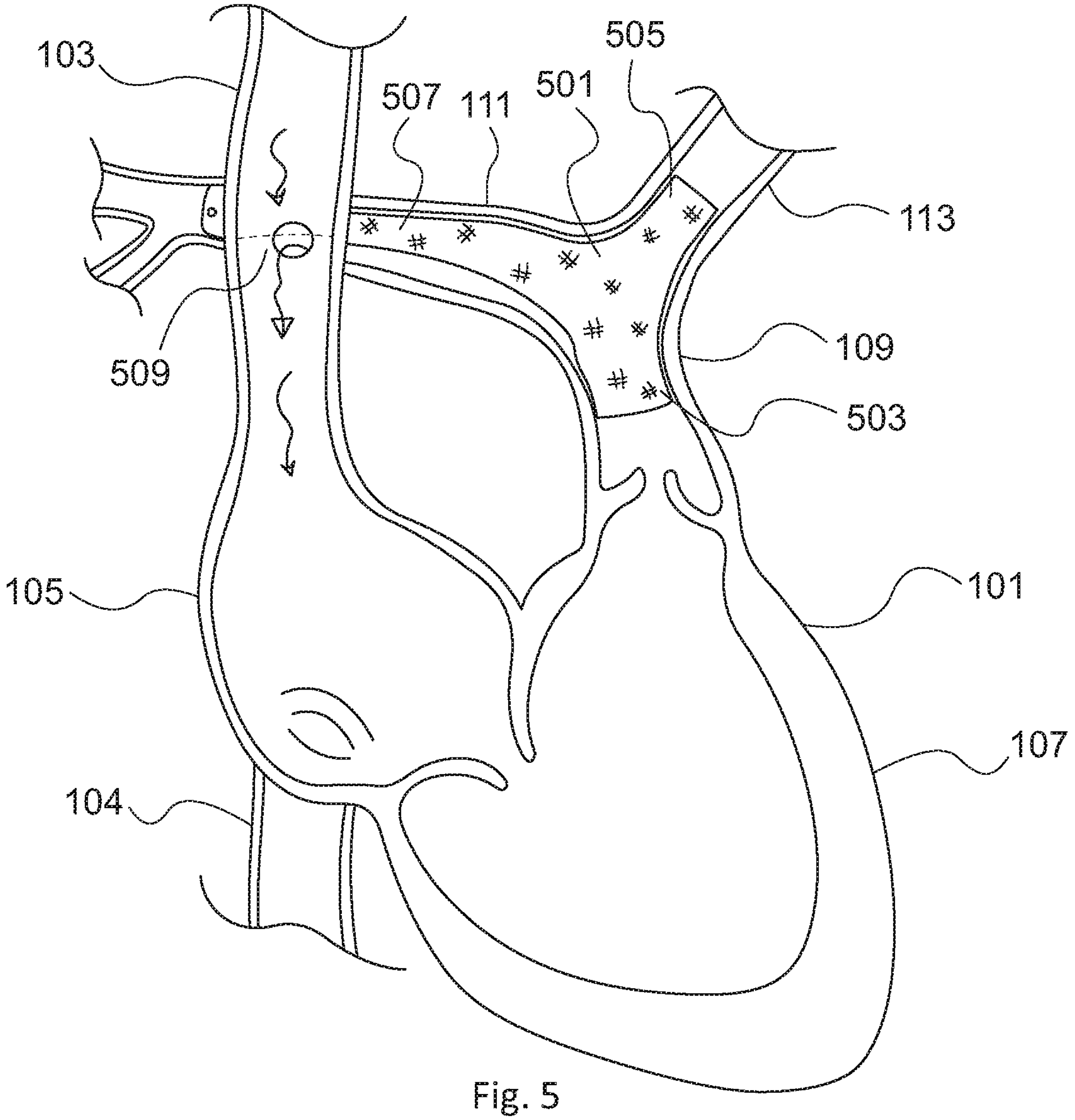
FIG. 5 illustrates an exemplary device implanted between the superior vena cava and pulmonary artery according to some embodiments of the present teachings.

Turning now to FIG. 5, embodiments of the present invention are depicted. A patient's heart 101 is shown in cross-section, including a superior vena cava (SVC) 103, a right atrium 105, an inferior vena cava 104, a right ventricle 107, and a pulmonary artery 109. The pulmonary artery includes a left branch 113 and a right branch 111. A compliant implant 501 resides in the pulmonary artery. The compliant implant includes a proximal section 503, a left branch 505, and a right branch 507. The compliant implant includes a generally cylindrical proximal anchoring section, as well as generally cylindrical left branch anchoring section and right branch anchoring sections. The compliant implant includes a reversibly collapsible and expandable segment. The reversibly collapsible segment extends from the right branch of the compliant implant and into the proximal section of the compliant implant. An arterio-venous shunt 509 has been formed between the pulmonary artery and the superior vena cava. This shunt could be created by any suitable means, including RF ablation, cutting, or puncturing and dilating. A shunting device similar to that described above may be implanted to maintain or create the shunt. The compliant implant may include a metallic or polymeric skeleton structure. The compliant implant may include a polymeric or biological covering material. In embodiments the compliant implant may be similar in construction to a bifurcated covered stent.

The compliant implant of FIG. 5 may function in a similar manner to the embodiments described above. For example, during the diastolic phase of the cardiac cycle the collapsible and expandable portion of the compliant implant is collapsed into the fluid diameter of the compliant implant. During the systolic phase of the cardiac cycle the collapsible and expandable portion of the compliant implant expands such that the wall of the implant is nearly in contact with the wall of the pulmonary artery. This action temporarily results in blood or saline being pushed from the pulmonary artery and into the superior vena cava. The result of the expansion and collapse of the compliant implant during a cardiac cycle is that the volumetric compliant of the pulmonary artery vasculature is substantially enhanced.

In embodiments, the device of FIG. 5 includes a compliant implant delivered into the superior vena cava. In some embodiments the compliant implant in the superior vena cava and the pulmonary artery together create a closed system where blood, saline, or another fluid is alternatively pushed from the superior vena cava and pulmonary artery as the pressure gradient changes between the two vessels.

In embodiments, the space between the compliant implant of FIG. 5 and the inner walls of the pulmonary artery are filled by a compliant balloon. In some embodiments the compliant balloon extends into the superior vena cava and create a haemodynamic seal between the two vessels. In some embodiments a multi-chambered compliant balloon fills the space around the compliant implant. The multiple chambers each extend from the pulmonary artery into the superior vena cava. The multiple chambers are configured to collapse and transfer fluid from the pulmonary artery to the SVC. The multiple chambers may be configured to allow more complete evacuation of the fluid form the pulmonary artery side of the implant. In embodiments the compliant implant has an inflation lumen incorporated into the walls of the implant. In embodiments the inflation lumen may be used to alter or adjust the stiffness of the reversible collapsible and expandable segment of the compliant implant.

Figure 6:
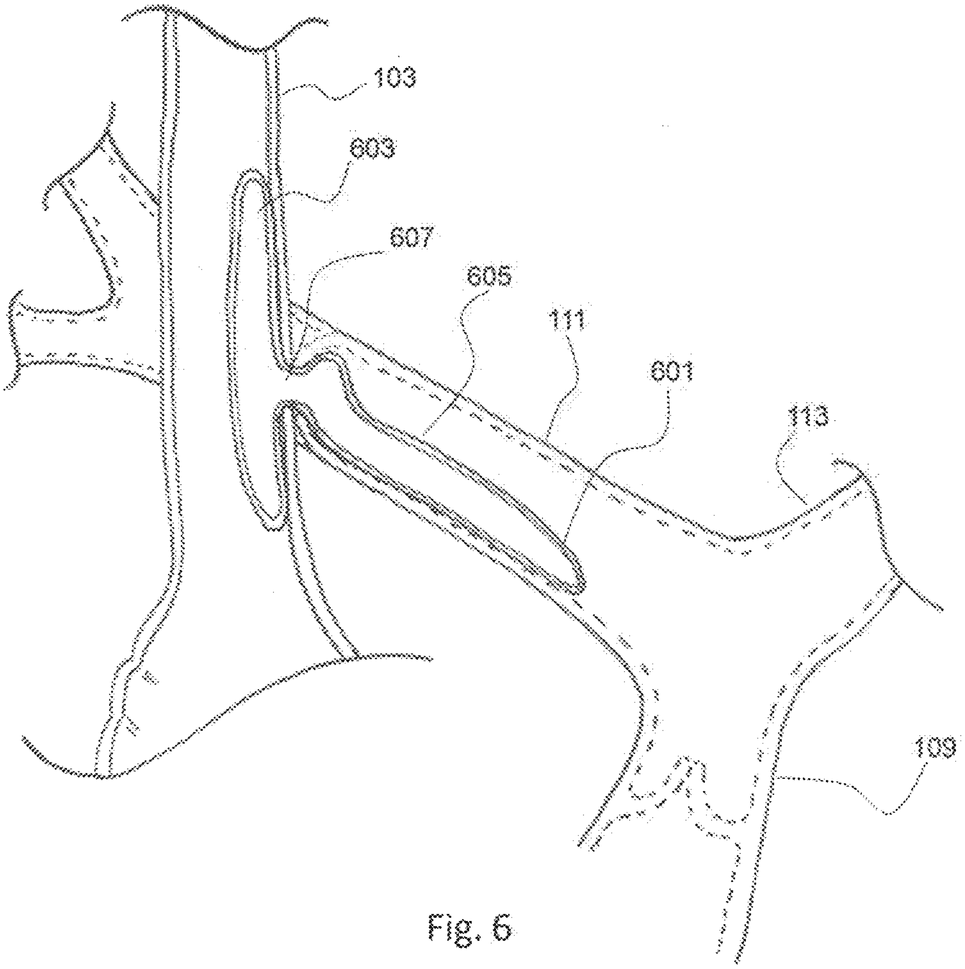
FIG. 6 illustrates an exemplary device implanted between the superior vena cava and pulmonary artery according to some embodiments of the present teachings.

Turning now to FIG. 6, embodiments of the present invention are depicted. A patient's superior vena cava 103 and pulmonary artery 109 are shown. The pulmonary artery includes a left branch 113 and a right branch 111. A connection has been made between the superior vena cava and the pulmonary artery. The connection may be made using any suitable devices or methods, including those described above and depicted in FIG. 1. A two chambered implantable balloon 601 is shown implanted into the pulmonary artery and SVC. The balloon includes a venous side 603, an arterial side 605, and a waist section 607. The waist section may be configured to substantially compress the walls of the pulmonary artery and SVC together in order to prevent blood flow around the device our outside the walls of the vessels. The waist section may be configured to be substantially more rigid than the rest of the balloon. The waist section of the balloon may incorporate features for adhering the balloon to the tissue, for example, ridges may be built into the surface of the balloon, or compressible fabric may be attached to the waist of the balloon. The waist section of the balloon may include hooks or similar structures for engaging the tissue. The arterial side of the balloon may feature any suitable shape, for example, an annular balloon may be used. The arterial side of the balloon is compliant and is configured to be reversibly collapsible. The arterial side of the balloon may extend into the pulmonary artery trunk or across and into the left branch of the pulmonary artery. The arterial aspect of the balloon is sized in order to provide sufficient volumetric compliance to treat pulmonary hypertension. For example, the arterial aspect of the balloon may contain about 25 mL of saline during the diastolic phase of the cardiac cycle and may collapse to a volume of about 10 mL during the systolic phase of the cardiac cycle. The venous side of the balloon may feature any suitable size or shape. For example, the venous side of the balloon may feature a hemi-cylindrical shape, or a crescent shape, or may simply be an elongate generally cylindrical shape. The venous side of the balloon is configured to be generally compliant. The venous side of the balloon is configured to expand at a known pressure differential and with pre-determined pressure-volume relationship effect. The venous side of the balloon may incorporate features designed to allow for rapid expansion of the balloon, for example, corrugations or folds may be incorporated into the shape of the balloon in order to facilitate the expansion of the balloon. The venous side of the balloon may be configured to expand from a first volume to a second larger volume with only minor changes in pressure. The venous side of the balloon may instead be configured to expand from a first volume to a second larger volume but only when subjected to a predetermined increase in pressure. The compliance behaviour of the balloon may be configured such that a desired and predetermined pressure-volume relationship is achieved. In embodiments the venous side of the balloon is compliant across a large range of inflated volumes, for example, from 20 mL to 40 mL. The venous side of the balloon may then be inflated as necessary to normalize the pressure on the arterial side of the balloon such that the arterial side of the balloon collapses during systole and expands during diastole. The balloon of FIG. 6 may be anchored to the SVC or the pulmonary artery by an optional stent-like anchor. The balloon of FIG. 6 may feature an elongate non-compressible skeleton structure along one edge of the balloon. For example, a steel ribbon may be incorporated into the wall of the balloon from the neck feature to the end of the balloon furthest from the neck feature. This ribbon may be configured to substantially stiffen the balloon in one direction, thereby preventing the balloon from changing shape due to the rush of blood during the cardiac cycle. In this manner the balloon chambers may be configured to expand and contract while substantially maintaining its general shape. The balloon of FIG. 6 may be inflated by a removable inflation device. The balloon of FIG. 6 may be inflated by a permanent or implantable inflation device which may be access in follow up procedures to further treat the patient.

The balloon of FIG. 6 may be made from any suitable material including polyurethane, latex rubber, PET, PE, or other suitable polymeric materials. The balloon may be inflated with any suitable fluid, including Saline, water, contrast medium, air, nitrogen, or helium.

Figure 7:
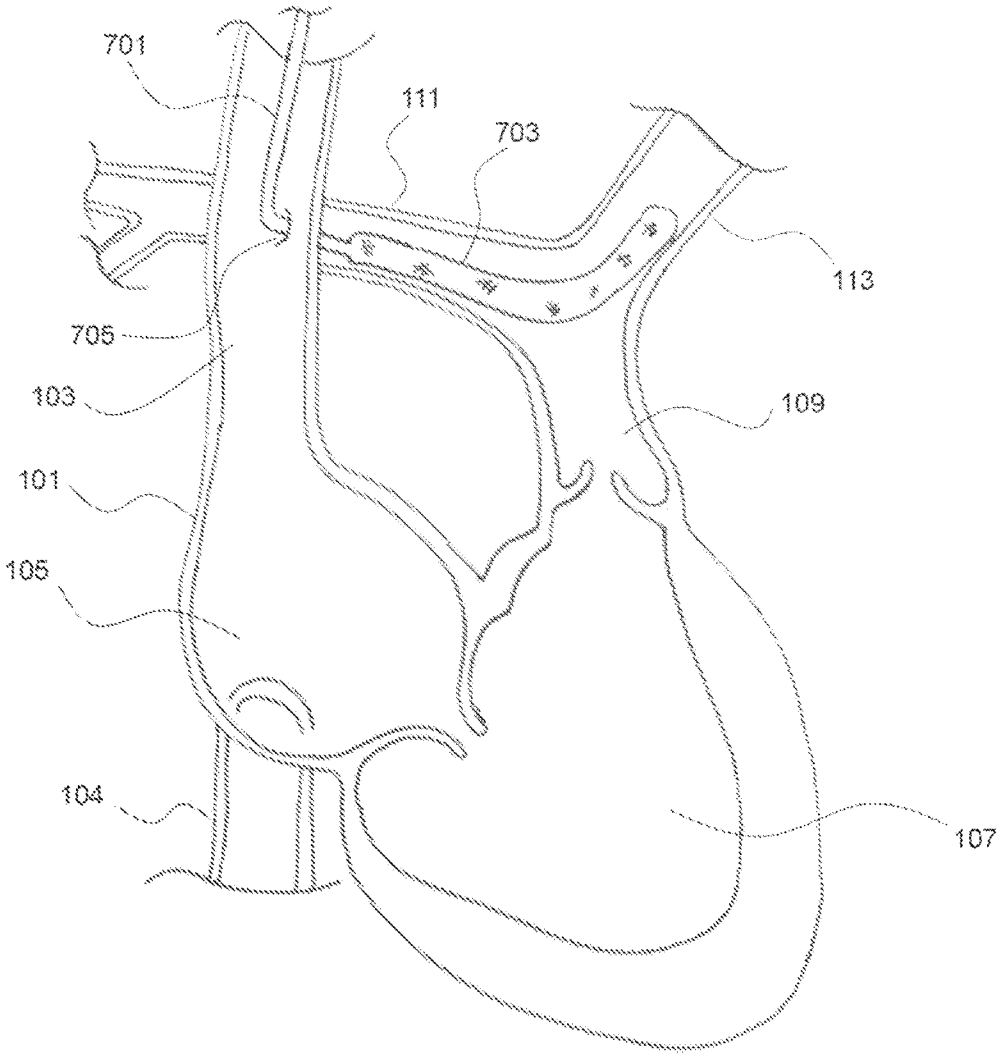
FIG. 7 illustrates an embodiment of the present teachings, where an exemplary elongate inflation lumen extends from the vasculature into the superior vena cava according to some embodiments of the present teachings.

Turning now to FIG. 7, embodiments of the invention are depicted. A cross-section of a patient's heart 101 is shown, including a superior vena cava 103, an inferior vena cava 104, a right atrium 105, a right ventricle 107, and a pulmonary artery 109. The pulmonary artery is split into a right branch 111 and a left branch 113. An elongate inflation lumen 701 extends from the vasculature into the superior vena cava and through an arterial-venous opening 705. The inflation lumen connects to compliant balloon 703.

In embodiments the inflation lumen 701 is connected to an electromechanical pump. The pump is configured to reversibly push a fluid through the lumen and into the balloon. The pump may be implantable, and may reside in the location typically reserved for pacemakers. The pump may be implanted in a similar manner to a pacemaker. In embodiments the balloon may include pressure sensing elements. In embodiments the balloon or inflation lumen may include electrical sensing elements, similar to that of an ECG lead. The pressure sensing and electrical sensing elements may be configured to electronically send the pressure and electrical information to the implantable pump. The implantable pump may be configured to use this information to determine, programmatically or algorithmically, when and how much fluid to pump into or out of the balloon. In embodiments the inflation lumen, balloon, and sensing elements may therefore act in a manner similar to an intra-aortic balloon pump. The balloon of FIG. 7 may include pre-folded creases in order to facilitate rapid inflation and deflation of the balloon. The balloon, pump, and inflation lumen may be configured to pump approximately 20 mL of fluid into and out of the balloon during the cardiac cycle. The fluid moved by the pump may be any suitable fluid, including saline or helium. In some embodiments the balloon, pump, and inflation lumen may be implanted simultaneously with a pacemaker lead or leads. In some embodiments a pacemaker and implantable pump are designed to work together to ensure that the timing of the balloon pulsation is optimal for increasing the effective arterial compliance by way of inflating and deflating the balloon. In some embodiments the inflation lumen is externalized through an implantable port and connected to an external inflation machine, similar to that of an inter-aortic balloon pump. In some embodiments the balloon, inflation lumen, and arterial-venous connection of FIG. 7 may be used in conjunction with an external pumping machine for emergency care following a sudden decrease in RV function. In some embodiments the balloon and inflation lumen is connected to an extra-corporal electronic pump. In some embodiments the balloon, inflation lumen, and external pump work in concert with an ECG in order to provide counter-pulsation and in order to lower the RV afterload in a patient. In some embodiments the invention as depicted in FIG. 7 may be used for temporary palliative care, for example, for treating a patient with severe right ventricular disfunction and congestive heart failure. In some embodiments the invention as depicted in FIG. 7 may be used as a bridge to recovery in a similar manner to left ventricular assist devices, where a patient who has undergone an acute cardiac event can have their RV afterload reduced and right sided cardiac output augmented temporarily allowing their RV to heal following an injury, such as a myocardial infarction.

What is claimed is:

1. A system for treating heart failure, the system comprising:

(A) a shunting device configured to be positioned across an opening created between a vein and a pulmonary artery, the shunting device comprising:

(i) a tubular body extending from a first end to a second end and having an internal lumen passing through the tubular body thereby forming a passage for fluid flow, (ii) a first plurality of anchoring arms extending from the first end of the tubular body, and (iii) a second plurality of anchoring arms extending from the second end of the tubular body, wherein the first plurality of anchoring arms and the second plurality of anchoring arms are configured to contact an inner wall of the pulmonary artery and an inner wall of the vein respectively to retain the shunting device in the opening between the vein and the pulmonary artery; and (B) a compliant implant extending from a proximal anchoring segment to a distal anchoring segment, wherein the compliant implant comprises a reversibly collapsible portion configured to transition between an expanded configuration having the reversibly collapsible portion substantially fill a space of the pulmonary artery and a collapsed configuration having the reversibly collapsible portion spaced apart from the shunting device, wherein the reversibly collapsible portion is configured to be keyed to the shunting device such that at least a portion of the reversibly collapsible portion of the compliant implant substantially faces the shunting device.

2. The system of claim 1, wherein a diameter of the internal lumen of the shunting device is between 4 mm and 10 mm.

3. The system of claim 1, wherein the shunting device comprises at least one of Nitinol, stainless steel, polyurethane, PET, PEEK, cobalt chromium alloys, a metallic material, an alloy, and a polymeric material.

4. The system of claim 1, wherein the shunting device is covered by a fabric or film configured to form a haemostatic seal against the inner wall of the pulmonary artery and the inner wall of the vein.

5. The system of claim 1, wherein the shunting device is configured to allow fluid to flow through the internal lumen of the shunting device and to prevent blood from passing around the first plurality of anchoring arms and the second plurality of anchoring arms of the shunting device.

6. The system of claim 1, wherein the shunting device protrudes into the pulmonary artery such that when the compliant implant expands due to a systolic pressure wave the expansion around the shunting device is limited, thereby allowing fluid to be forced through the shunting device and preventing the compliant implant from prematurely closing off the fluid path created by the shunting device.

7. The system of claim 1, wherein the shunting device is configured to be delivered over a wire passed through the opening.

8. The system of claim 1, wherein the shunting device is configured to be delivered from the vein and/or the pulmonary artery.

9. A system for treating heart failure, the system comprising:

(A) a shunting device configured to be positioned across an opening created between a vein and a pulmonary artery; and (B) a compliant implant extending from a proximal anchoring segment to a distal anchoring segment, the compliant implant comprising:

(i) a round wall segment, (ii) a substantially flattened wall segment having at least a portion which is configured to reversibly transition between a collapsed configuration and an expanded configuration, wherein at least a portion of the substantially flattened wall segment faces the shunting device, and (iii) a center lumen passing through a longitudinal axis of the compliant implant, wherein the substantially flattened wall segment is configured to transport fluid from the center lumen through the shunting device when in the expanded configuration and to prevent fluid flow from the center lumen through the shunting device when in the collapsed configuration.

10. The system of claim 9, wherein the compliant implant comprises a laser cut hypotube which has been heat set into a desired shape.

11. The system of claim 9, wherein the compliant implant comprises or is surrounded by a wall of hydrogel material.

12. The system of claim 9, wherein the compliant implant comprises a covering material composed of a sheath of expanded PTFE polymer.

13. The system of claim 9, further comprising at least one tubular extrusion extending from a wall of the compliant implant.

14. The system of claim 13, further comprising a stiffening bar configured to adjust a pressure differential required to collapse and expand the compliant implant.

15. The system of claim 14, wherein the stiffening bar comprises a material selected from the group consisting of stainless steel, Nitinol, polyether ether ketone (PEEK), polyimide, polyurethane, polytetrafluoroethylene (PTFE), fluorinated ethylene propylene (FEP), ultra-high molecular weight polyethylene, cobalt-chromium alloy, a metallic alloy, a polymeric material, and a combination of two or more thereof.

16. The system of claim 9, wherein the proximal anchoring segment and the distal anchoring segment each have a generally round cylindrical shape and are configured to form a seal with an inner wall of a blood vessel so as to prevent fluid from flowing from one end of the blood vessel around the compliant implant.

17. The system of claim 9, wherein the substantially flattened wall segment is configured to retain a collapsed configuration having a flattened shape under a first amount of internal blood pressure and to reversibly transition to the expanded configuration having a rounded shape under a second amount of internal blood pressure that is higher than the first amount of internal blood pressure.

18. The system of claim 17, wherein the first and second amounts of internal blood pressures are adjustable by incorporating pull wires and/or stiffening wires into the structure of the compliant implant.

19. The system of claim 9, wherein the shunting device is configured to be delivered over a wire passed through the opening.

20. The system of claim 9, wherein a diameter of the internal lumen of the shunting device is between 4 mm and 10 mm.

* * * * *